United States Patent
Gabele et al.

(10) Patent No.: US 9,351,777 B2
(45) Date of Patent: May 31, 2016

(54) MEDICAL SYNTHESIS SYSTEM AND METHOD OF CONNECTING A MULTIPART MEDICAL SYNTHESIS SYSTEM

(75) Inventors: Lorenz Gabele, Sauldorf (DE); Frank Reinauer, Lieptingen (DE)

(73) Assignee: Karl Leibinger Medizintechnik GmBH & Co. KG, Muhlheim (DE)

( * ) Notice: Subject to any disclaimer, the term of this patent is extended or adjusted under 35 U.S.C. 154(b) by 1317 days.

(21) Appl. No.: 12/220,243

(22) Filed: Jul. 23, 2008

(65) Prior Publication Data
US 2009/0143780 A1 Jun. 4, 2009

(30) Foreign Application Priority Data
Jul. 23, 2007 (DE) .................. 10 2007 034 169

(51) Int. Cl.
A61B 17/00 (2006.01)
A61B 17/80 (2006.01)
A61B 17/32 (2006.01)
A61B 17/86 (2006.01)

(52) U.S. Cl.
CPC ......... *A61B 17/8085* (2013.01); *A61B 17/8033* (2013.01); *A61B 17/320068* (2013.01); *A61B 17/866* (2013.01); *A61B 2017/00004* (2013.01); *A61B 2017/00831* (2013.01); *A61B 2017/00902* (2013.01); *A61B 2017/00955* (2013.01)

(58) Field of Classification Search
USPC ........................................................ 606/280
See application file for complete search history.

(56) References Cited

U.S. PATENT DOCUMENTS

| | | | | |
|---|---|---|---|---|
| 5,163,960 A | * | 11/1992 | Bonutti | 128/898 |
| 5,234,431 A | * | 8/1993 | Keller | 606/70 |
| 5,607,427 A | * | 3/1997 | Tschakaloff | 606/284 |
| 5,868,746 A | * | 2/1999 | Sarver et al. | 606/281 |
| 7,524,323 B2 | * | 4/2009 | Malandain | 606/246 |
| 7,967,820 B2 | * | 6/2011 | Bonutti et al. | 606/64 |
| 8,974,503 B2 | * | 3/2015 | Brunner et al. | 606/281 |
| 9,017,380 B2 | * | 4/2015 | Mayer et al. | 606/232 |
| 2001/0002439 A1 | * | 5/2001 | Bonutti et al. | 606/232 |
| 2002/0022843 A1 | * | 2/2002 | Michelson | 606/70 |
| 2002/0129820 A1 | * | 9/2002 | Ryan et al. | 128/858 |
| 2004/0030341 A1 | * | 2/2004 | Aeschlimann et al. | 606/72 |
| 2005/0216008 A1 | | 9/2005 | Zwirnmann et al. | |
| 2006/0089646 A1 | * | 4/2006 | Bonutti | 606/61 |
| 2008/0312698 A1 | * | 12/2008 | Bergeron et al. | 606/280 |

FOREIGN PATENT DOCUMENTS

EP 455255 * 6/1991 ............ A61B 17/58
EP 1363543 9/2006

* cited by examiner

*Primary Examiner* — Christian Sevilla
(74) *Attorney, Agent, or Firm* — Dilworth & Barrese, LLP

(57) ABSTRACT

The invention relates to a medical synthesis system as well as to a method of connecting a multipart medical synthesis system. The medical synthesis system in this respect includes at least one supporting element and at least one synthesis element, wherein the supporting element is provided for fastening in an organic structure. In this respect, the synthesis element is provided for the fastening to the already fastened supporting element. The synthesis element and the supporting element form a non-releasable coherent unit during application.

13 Claims, 2 Drawing Sheets

MEDICAL SYNTHESIS SYSTEM AND METHOD OF CONNECTING A MULTIPART MEDICAL SYNTHESIS SYSTEM

BACKGROUND OF THE INVENTION

The invention relates to a medical synthesis system as well as to a method of connecting a multipart medical synthesis system in accordance with the description herein.

Multipart medical synthesis systems are known from the prior art. These already known systems usually consist of supporting or fixing elements such as screws or nails as well as synthesis plates. Such systems can be used, for example, for the purpose of connecting bone fragments to one another. Previously, for this purpose, the synthesis plate has been placed onto the bone fragments to be connected and has been fastened by means of screws or nails. However, this has the disadvantage that the position of the synthesis plate cannot be changed due to the fastening. Even a great deal of experience of the person making the attachment cannot avoid such inaccuracies in certain cases since the spatial access to as well as the view of the synthesis system to be fastened is usually greatly restricted.

SUMMARY OF THE INVENTION

It is therefore the object of the present invention to further develop a medical synthesis system to the effect that the connection of the components of the medical synthesis system can be carried out with the greatest possible accuracy even under tight spatial conditions as well as under poor visibility conditions.

This object is solved by a medical synthesis system having the features herein. Provision is accordingly made for the medical synthesis system to include at least one supporting element and at least one synthesis element, with the supporting element being provided for fastening in an organic structure. In this respect, the synthesis element is provided for the fastening to the already fastened supporting element. The synthesis element and the supporting element form a non-releasable coherent unit during the application.

The term "during the application" in this respect designates the time period from the installation of the medical synthesis system until the removal of the same or until the resorption of at least parts of the medical synthesis system. Furthermore, it is assumed for the definition of the term that no external influences result in the failure of the system during the application.

A medical synthesis system having the features of claim 1 thus has the advantage that initially e.g. a plurality of supporting elements such as screws can be positioned and fastened very accurately. In accordance with the invention, a synthesis plate is then attached to the already fastened screws, preferably to the screw heads. Such a connection can be realized simply, fast and securely. Such a system permits an assembly with the greatest possible positioning accuracy in a very tight space even with low visibility. Such a synthesis system can naturally be used for the purposes of medical education and further education.

Transferred to the specific case of osteosynthesis, a minimally invasive and highly accurate positioning thus becomes possible. This is moreover accompanied by a significant saving in time. A time saving In the health care system is moreover accompanied by high cost savings since, on the one hand, the capacity of rooms such as operating rooms is used better and, on the other hand, a team of several persons is also always involved in an osteosynthesis procedure.

Provision can furthermore be made for the synthesis element to be fastened to the supporting element by means of a connection formed by energy input and/or by heat and/or by ultrasonic welding and/or by friction. The advantage thereby results that a connection can be established fast and reliably. This connection can also simultaneously be established exactly at a predefined position. Welding processes are already known in the medical sector for the preparation of such connections which have already proved themselves in the corresponding circumstance.

The synthesis element can be fastened to the supporting element, with the connection of the two elements being established by using an auxiliary material. A resorbable or a non-resorbable biocompatible material can be introduced between the synthesis element as well as the supporting element in this case. The components are connected by energy input and/or by heat and/or by ultrasonic welding and/or by friction. The advantage thereby results of being able to weld components of a synthesis system to one another which comprise a different material and at least a material which cannot be welded. A weld connection is then e.g. possible by the auxiliary material.

The supporting element can furthermore be fastened in the organic structure by screwing or driving or welding. This enables a highly accurate positioning of the supporting element The so-called "sonic weld process" can be the welding method for example. Provision can be made in this respect for the supporting element to be a screw, a pin or a nail.

It is particularly. advantageous for the supporting element to comprise a resorbable material. Resorption of the supporting element can make a removal after the application superfluous. It is stated by way of example for osteosynthesis that when the system in accordance with the invention is used, an improved and faster healing is possible due to reduced surgical trauma and a removal can be dispensed with in the case of the use of resorbable materials.

The synthesis element can be made as a plate or as a film or as a membrane or as a mesh. A plate has the advantage, for example, that fragments to be connected can remain securely connected to one another during the application.

It is furthermore conceivable for the synthesis element to comprise a thermoplastic material. Thermoplastic materials have the advantage that firmly bonded connections can be realized with them as a consequence of heat input.

It is of particular advantage if the synthesis elements comprises a transparent material. It thereby becomes possible for the person connecting the synthesis system first to position the synthesis elements relative to the supporting elements and to realize the weld connection, e.g. by means of ultrasonic welding, after the exact positioning.

The synthesis element can furthermore comprise a resorbable material. The advantage in particular results in combination with resorbable supporting elements that a specific removal can be dispensed with. It is furthermore advantageous that resorbable materials for medical applications have high biocompatibility and at least some materials are thermoplastic. A plurality of the aforesaid advantages are thus combined. The components can in particular be connected directly to one another in a firmly bonded manner in addition to the exact positioning.

The advantage results for the use as an osteosynthesis system that, in addition to an exact fixing of bone fragments or in addition to the replacement of missing fragments or organic structures by the resorbable material, the time of the required application can be reduced.

The invention furthermore relates to a method of connecting a multipart medical synthesis system comprising at least one supporting element, with the supporting element being provided for fastening in an organic structure and comprising at least one synthesis element, the synthesis element being connected coherently and non-releasably for the application to the already fastened supporting element.

The advantages of the method are produced, for example, after the positioning of the supporting elements. In accordance with the invention, a synthesis plate can e.g. be attached to the already fastened screws, preferably to the screw heads, with a small effort and/or cost. Such a system permits a fast and secure assembly with the greatest possible positioning accuracy in a very tight space even with difficult visibility conditions.

The synthesis element can be fastened to the supporting element by means of energy input by heat and/or by ultrasonic welding and/or by friction. This enables a fast and secure firmly bonded connection.

It is possible to fasten the synthesis element to the supporting element by means of a resorbable or of a non-resorbable biocompatible material as well as by energy input and/or by heat and/or by ultrasonic welding andlor by friction. For example, materials which cannot be connected to one another by welding can thus be connected to one another fast and securely while using an auxiliary material.

BRIEF DESCRIPTION OF THE DRAWINGS

Further details and advantages of the invention will be explained in more detail with reference to an embodiment shown in the drawing.

There are shown.

DESCRIPTION OF THE PREFERRED EMBODIMENTS

Figure 1:
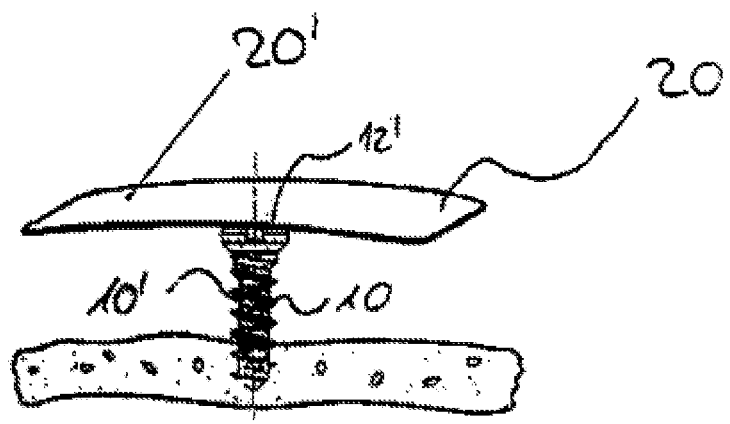
FIG. 1 a side view of the medical synthesis system in accordance with the invention.

FIG. 1 shows the medical synthesis system in accordance with the invention in an embodiment with a screw 10' as the supporting element 10. The screw 10' of resorbable thermoplastic is already fastened in this respect. The synthesis element 20 made as a synthesis plate 20' is welded onto the screw head 12'. The synthesis plate 20' in this respect is made of a transparent and resorbable thernoplastic. This enables an exact, fast and secure positioning of the synthesis-plate 20' relative to the screw 10'.

Figure 2:
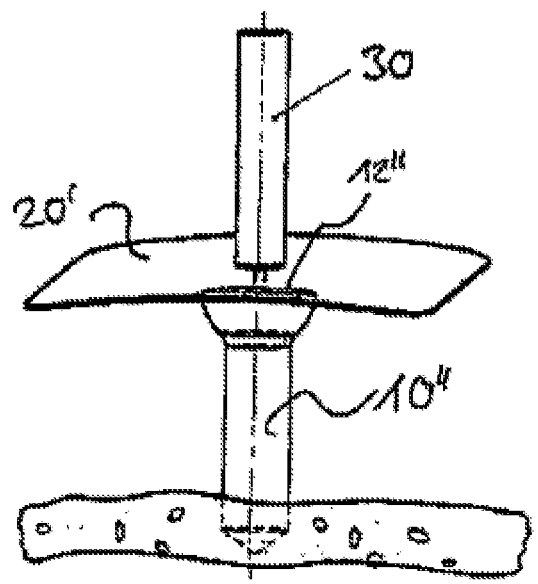
FIG. 2 a side view of the medical synthesis system in accordance with the invention with an ultrasonic welding head.

FIG. 2 shows the medical synthesis system in accordance with the invention in an embodiment with a pin 10" as the supporting element. This pin 10" is likewise made of a resorbable thermoplastic. The synthesis plate 20' is welded onto the head 12" of the pin 10" by means of an ultrasonic welding head 30. The temperatures arising in this process are not critical for the surrounding structures in this respect. In this connection, the synthesis plate 20' is made of a transparent, resorbable thermoplastic, which enables an exact positioning of the welding head 30, synthesis plate 20' and pin 10".

Figure 3:
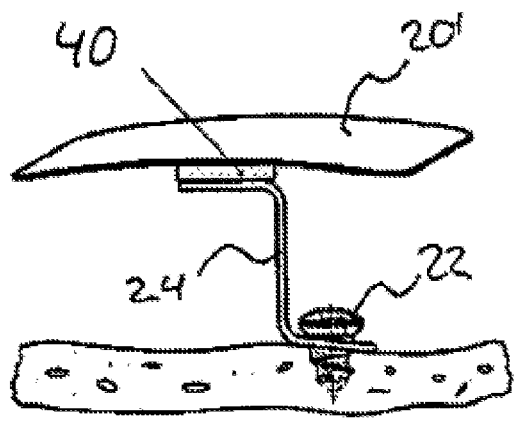
FIG. 3 a side view of the synthesis system, with the connection between the supporting element and the synthesis element being established by means of an auxiliary material.

The embodiment is shown in FIG. 3 in which a separate auxiliary material 40 of thermoplastic biocompatible material is required for the connection of the components of the medical synthesis system. The supporting element in this respect comprises a screw 22 as well as a holding hoop 24 made of a metal alloy, with the holding hoop 24 not being able to be securely welded to the synthesis plate without the auxiliary material 40. The synthesis plate 20' in this embodiment comprises a biocompatible thermoplastic.

Figure 4:
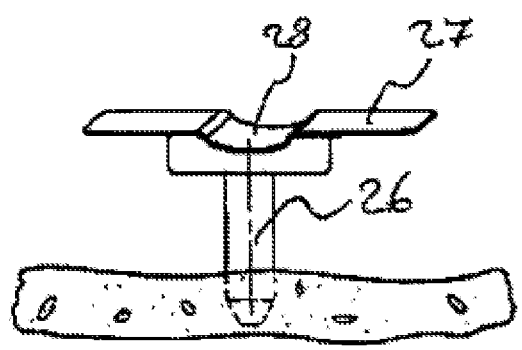
FIG. 4 a side view of a supporting element with a fastening surface.

A side view of a supporting element is shown in FIG. 4 in the embodiment as a pin 26 with a fastening surface 27. The fastening surface 27 in this connection enables the secure support of a synthesis element, with a recess 28 additionally being provided in the fastening surface 27 for the reception of auxiliary materials or of the plastically deformed material.

The invention claimed is:

1. A medical synthesis system having at least one supporting element (10) and at least one synthesis element (20), wherein
    the supporting element (10) is provided for fastening in an organic structure and is a screw (10', 22), pin (10", 26) or nail, and
    the synthesis element (20) is non-releasably secured directly to a top of and entirely covering the top of a head (12', 12") of the screw (10'), pin (10", 26) or nail, and with the top of the head (12', 12") completely abutting a closed surface of the synthesis element (20),
    such that the synthesis element (20) is securable to the supporting element (10) after the supporting element (10) has already been fastened in the organic structure and the synthesis element (20) and supporting element (10) form a non-releasable coherent unit during application to the organic structure, and
    the synthesis element (20) is fastened to the supporting element (10) by a connection formed by energy input and/or by heat and/or by ultrasonic welding and/or by friction, wherein the synthesis element (20) includes a recess on a side opposite the screw (10'). pin (10", 26) or nail.

2. A medical synthesis system in
    accordance with claim 1, wherein the synthesis element is fastened to the supporting element by a connection formed by resorbable or a non-resorbable biocompatible material as well as by energy input and/or by heat and/or by ultrasonic welding and/or by friction.

3. A medical synthesis system in
    accordance with claim 1, wherein the supporting element is fastened in the organic structure by screwing or driving or welding.

4. A medical synthesis system in accordance with claim 1, wherein the supporting element comprises a biocompatible material.

5. A medical synthesis system having at least one supporting element (10) and at least one synthesis element (20), wherein the supporting element (10) is provided for fastening in an organic structure and is a screw (10', 22), pin (10", 26) or nail,
    the synthesis element (20) is non-releasably secured directly to a top of and entirely covering the top of a head (12', 12") of the screw (10'), pin (10", 26) or nail, and with the top of the head (12', 12") completely abutting a closed surface of the synthesis element (20),
    such that the synthesis element (20) is securable to the supporting element (10) after the supporting element (10) has already been fastened in the organic structure and the synthesis element (20) and supporting element (10) form a non-releasable coherent unit during application to the organic structure, the synthesis element (20) is fastened to the supporting element (10) by a connection formed by energy input and/or by heat and/ or by ultrasonic welding and/or by friction, wherein the synthesis element (20) includes a recess on a side opposite the screw (10'), pin (10", 26) or nail, and the supporting element (10) comprises a resorbable material.

6. A medical synthesis system in accordance with claim 1, wherein the synthesis element is made as a plate or as a film or as a membrane or as a mesh.

7. A medical synthesis system in accordance with claim 1, wherein the synthesis element comprises a thermoplastic material.

8. A medical synthesis system in accordance with claim 1, wherein the synthesis element comprises a transparent material.

9. A medical synthesis system in accordance with claim 1, wherein the synthesis element comprises a resorbable material.

10. A medical synthesis system in accordance with claim 1, wherein the synthesis element (20) is configured to be non-releasably secured to the screw (10'), pin (10", 26) or nail in the absence of any additional separate clamping element.

11. A medical synthesis system in accordance with claim 1, wherein the synthesis element (20) is configured to be non-releasably secured to the screw (10'), pin (10", 26) or nail from only one direction above the second end of the head (12', 12") of the screw (10'), pin (10", 26) or nail.

12. A medical synthesis system in accordance with claim 1, wherein the synthesis element (20) is configured to be non-releasably secured to the screw (10'), pin (10", 26) or nail in the absence of securing adjacent screws (10'), pins (10", 26) or nails to each other.

13. A medical synthesis system in accordance with claim 1, wherein the synthesis element (20) is configured to be non-releasably secured to and cover only a very top of the second end of the screw (10'), pin (10", 26) or nail.

* * * * *